US00PP21458P2

(12) United States Plant Patent
Bergman

(10) Patent No.: US PP21,458 P2
(45) Date of Patent: Nov. 9, 2010

(54) ***CHRYSANTHEMUM* PLANT NAMED 'BRONZE YOCHATHAM'**

(50) Latin Name: *Chrysanthemum×morifolium*
Varietal Denomination: Bronze Yochatham

(75) Inventor: Wendy R. Bergman, Lehigh Acres, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/586,652

(22) Filed: Sep. 25, 2009

(51) Int. Cl.
*A01H 5/00* (2006.01)

(52) U.S. Cl. ..... Plt./296

(58) Field of Classification Search ..... Plt./296
See application file for complete search history.

*Primary Examiner*—Annette H Para
(74) *Attorney, Agent, or Firm*—S. Matthew Edwards

(57) ABSTRACT

A new *Chrysanthemum* plant named 'Bronze Yochatham,' particularly distinguished by the medium sized, greyed-orange ray florets, good floriferousness, compact and easily controlled uniform habit with excellent branching, and dark foliage.

1 Drawing Sheet

Latin name of the genus and species of the plant claimed: *Chrysanthemum×morifolium.*

Varietal denomination: 'Bronze Yochatham'.

BACKGROUND OF THE NEW PLANT

The present invention comprises a new *Chrysanthemum*, botanically known as *Chrysanthemum×morifolium*, and hereinafter referred to by the variety name 'Bronze Yochatham'.

'Bronze Yochatham' is a product of a planned breeding program. The new cultivar has medium sized, greyed-orange ray florets, good floriferousness, compact and easily controlled uniform habit with excellent branching, and dark foliage.

'Bronze Yochatham' originates as a natural whole plant mutation of 'Yochatham,' U.S. Plant Pat. No. 17,927. 'Bronze Yochatham' was discovered and selected by the inventor as a single flowering plant within a population of the parent cultivar grown outdoors in a field covered by saran in Fort Myers, Fla., in March 2005. The parent cultivar 'Yochatham' has light purple floret color. 'Yochatham' has a taller plant habit, smaller foliage size, and more ray florets than 'Bronze Yochatham'.

The first act of asexual reproduction of 'Bronze Yochatham' was accomplished when vegetative cuttings were propagated from the initial selection in March 2005 in a controlled environment in Fort Myers, Fla.

A Plant Breeder's Right for this cultivar was applied for in Canada in October 2008. 'Bronze Yochatham' has not been made publicly available more than one year prior to the filing of this application.

BRIEF SUMMARY OF INVENTION

Horticultural examination of plants grown from cuttings of the plant initiated in March 2005, and continuing thereafter, has demonstrated that the combination of characteristics as herein disclosed for 'Bronze Yochatham' are firmly fixed and are retained through successive generations of asexual reproduction.

'Bronze Yochatham' has not been observed under all possible environmental conditions. The phenotype may vary significantly with variations in environment such as temperature, light intensity and day length.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Bronze Yochatham' with colors being as true as possible with an illustration of this type. The photographic drawing shows four flowering potted plants of the new variety growing in a five inch pot, and a close-up of the flowers.

DETAILED BOTANICAL DESCRIPTION

The plant descriptions, measurements and aforementioned photographs were taken in Gilroy, Calif. in April 2009 under greenhouse conditions. These plants were started and grown in central coastal California, then shipped to Gilroy, Calif. in April 2009. Plants were grown under conditions which approximate those generally used in commercial potted *chrysanthemum* production and were about 9 weeks of age. Color references are made to The Royal Horticultural Society Colour Chart (R.H.S.) 2001.

TABLE 1

DIFFERENCES BETWEEN THE NEW VARIETY 'BRONZE YOCHATHAM' AND A SIMILAR VARIETY

| | 'Bronze Yochatham' | 'Amber Pomona' (U.S. Plant Pat. No. 12,248) |
|---|---|---|
| Flower color | Greyed-orange | Light orange-bronze |
| Plant height/width | Shorter/narrower | Taller/wider |
| Floriferousness | More | Slightly fewer |

Plant:
*Form, growth and habit.*—Herbaceous pot-type; compact but upright, freely branching. Suitable for production-center budded or no bud removal.
*Plant height.*—15-17 cm.
*Plant height (inflorescence included).*—20-21 cm.
*Plant width.*—16-19 cm.
Roots:
*Number of days to initiate roots.*—4 days at about 22 degrees C.
*Number of days to produce a rooted cutting.*—10 days at 22 degrees C.
*Type.*—Fine, fibrous, free branching.
*Color.*—RHS N155B but whiter.
Foliage:
*Arrangement.*—Alternate, simple.
*Immature, leaf color, upper surface.*—Closest to RHS 147A.
*Lower surface.*—Little darker than RHS 147B.
*Mature, leaf color, upper surface.*—Lighter than RHS 147A.
*Lower surface.*—Little darker than RHS 147B.
*Length.*—5.9-6.5 cm.
*Width.*—3.9-4.1 cm.
*Shape.*—Ovate.
*Base shape.*—Attenuate.
*Apex shape.*—Mucronulate.
*Margin.*—Palmately lobed; somewhat serrate.
*Texture, upper surface.*—Bi-fid T-shaped hairs.
*Lower surface.*—Bi-fid T-shaped hairs.
*Color of veins, upper surface.*—Closest to RHS 146C.
*Color of veins, lower surface.*—Closest to RHS 147C.
*Petiole color.*—RHS 146C.
*Length.*—0.8 cm.
*Diameter.*—0.2 cm.
*Texture.*—Bi-fid T-shaped hairs.
Stem:
*Quantity of main branches per plant.*—3-4.
*Quantity of leaves per branch.*—14-16.
*Color of stem.*—RHS 146B, but appear lighter with all the hairs.
*Length of stem.*—12-14 cm.
*Diameter.*—0.4 cm.
*Length of internodes.*—0.3-1.5 cm.
*Texture.*—Bi-fid T-shaped hairs.
*Color of peduncle.*—RHS 146B.
*Length of peduncle.*—3.8-7.5 cm.
*Peduncle diameter.*—0.15 cm.
*Texture.*—Bi-fid T-shaped hairs.
Inflorescence:
*Type.*—Composite type, solitary inflorescences (decorative-type) borne terminally above foliage, ray florets arranged acropetally on a capitulum.
*Quantity of short days to flowering (response time).*—48-54 days on center budded plants.
*Quantity of inflorescences per plant.*—8-10.
*Lastingness of individual blooms on the plant.*—About 32 days.
*Fragrance.*—Moderate.
Bud (just before opening/showing color):
*Color.*—Little lighter than RHS 176B.
*Length.*—1-1.4 cm.
*Width.*—0.9-1.1 cm.
*Shape.*—Oblate.
Immature inflorescence:
*Diameter.*—3.5-4.0 cm.
*Color of ray florets, upper surface.*—RHS 12C ground color; heavily overlaid with RHS 172B and RHS 172C.
*Lower surface.*—RHS 162B ground color; overlaid with RHS 172C.
Mature inflorescence:
*Diameter.*—5.6-6.2 cm.
*Total diameter of 'disc'.*—0.5 cm.
Ray florets:
*Average quantity of florets.*—About 150.
*Color of florets, upper surface.*—RHS 162B ground color, heavy overlaid and mottled between RHS 172C and RHS N170B giving almost a 'plaid' pattern effect; hues are brighter basally.
*Lower surface.*—RHS 162B ground color; overlaid with RHS 172C.
*Length.*—2.8-2.9 cm.
*Width.*—0.6-0.9 cm.
*Shape.*—Oblong to elliptical.
*Apex shape.*—Rounded to sometimes slightly retuse.
*Margin.*—Entire.
*Texture, upper surface.*—Papillose.
*Lower surface.*—Papillose.
Disc florets:
*Average quantity of florets.*—25-35.
*Color of florets.*—RHS 9A; RHS 1C basally.
*Length.*—0.7 cm.
*Width.*—0.1 cm.
*Shape.*—Tubular, enlongated.
*Apex shape.*—Acute, 5 pointed.
Phyllaries:
*Quantity.*—About 20.
*Color, upper surface.*—RHS 147B, lighter at margins which become papery.
*Lower surface.*—RHS 147B, lighter at margins which become papery.
*Length.*—0.5-0.6 cm.
*Width.*—0.2 cm.
*Shape.*—Lanceolate.
*Apex shape.*—Acute.
*Based.*—Fused.
*Margins.*—Entire; papery and opaque.
*Texture, upper surface.*—Glossy and smooth.
*Lower surface.*—Bi-fid T-shaped hairs.
Reproductive organs:
*Pistil.*—1.
*Length.*—0.6 cm.
*Style color.*—RHS 1C.
*Style length.*—0.5 cm.
*Stigma color.*—RHS 1B.
*Stigma shape.*—Bi-parted.
*Ovary color.*—RHS 155C.
*Stamens.*—4.
*Color of filaments.*—RHS 1C.
*Length filaments.*—0.2 cm.
*Anther color.*—RHS 12C.
*Anther length.*—0.1 cm.
*Anther shape.*—Oblong.
*Color of pollen.*—RHS 14A.
*Pollen amount.*—Scarce.
*Fertility/seed set.*—Has not been observed on this hybrid.
Disease/pest resistance: Disease resistance or susceptibility has not been observed on this hybrid.

What is claimed is:

1. A new and distinct variety of *Chrysanthemum* plant named 'Bronze Yochatham,' substantially as illustrated and described herein.

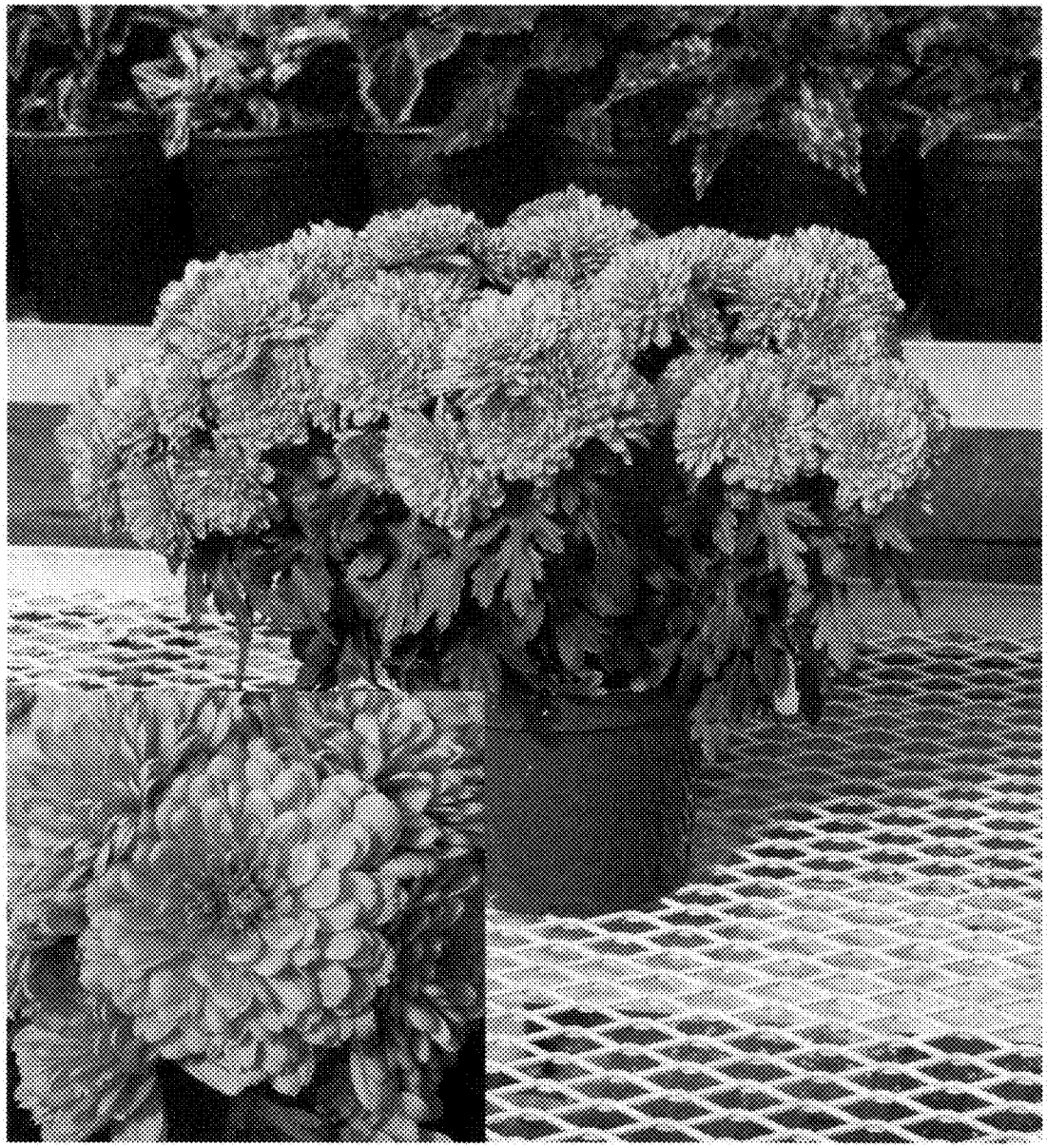

* * * * *